(12) United States Patent
Merkel et al.

(10) Patent No.: US 9,290,438 B2
(45) Date of Patent: Mar. 22, 2016

(54) METHOD FOR STARTING A REACTION DURING THE PRODUCTION OF AROMATIC AMINES FROM NITROAROMATICS

(71) Applicant: Bayer MaterialScience AG, Leverkusen (DE)

(72) Inventors: Michael Merkel, Dusseldorf (DE); Thomas Knauf, Dormagen (DE); Cliff Andre Peters, Schmedeswurth (DE); Thorsten Schmidt, Nindorf (DE)

(73) Assignee: Bayer MaterialScience AG, Leverkusen (DE)

( * ) Notice: Subject to any disclaimer, the term of this patent is extended or adjusted under 35 U.S.C. 154(b) by 5 days.

(21) Appl. No.: 14/394,139

(22) PCT Filed: Apr. 12, 2013

(86) PCT No.: PCT/EP2013/057717
§ 371 (c)(1),
(2) Date: Oct. 13, 2014

(87) PCT Pub. No.: WO2013/156410
PCT Pub. Date: Oct. 24, 2013

(65) Prior Publication Data
US 2015/0080611 A1     Mar. 19, 2015

(51) Int. Cl.
*C07C 209/36* (2006.01)
*C07C 209/84* (2006.01)

(52) U.S. Cl.
CPC ............ *C07C 209/36* (2013.01); *C07C 209/84* (2013.01); *Y02P 20/584* (2015.11)

(58) Field of Classification Search
CPC ........................... C07C 209/36; C07C 209/84
See application file for complete search history.

(56) References Cited

U.S. PATENT DOCUMENTS

| | | | |
|---|---|---|---|
| 3,136,818 A | 6/1964 | Sperber et al. | |
| 3,684,740 A | 8/1972 | Cimbalo et al. | |
| 4,265,834 A | 5/1981 | Birkenstock et al. | |
| 4,714,689 A | 12/1987 | Stammann et al. | |
| 5,808,157 A | 9/1998 | Langer et al. | |
| 5,877,350 A | 3/1999 | Langer et al. | |
| 6,043,394 A | 3/2000 | Langer et al. | |
| 6,521,791 B1 | 2/2003 | Welp et al. | |
| 8,044,244 B2 | 10/2011 | Seidemann et al. | |
| 2008/0234518 A1 | 9/2008 | Sommer et al. | |
| 2013/0131384 A1 | 5/2013 | Merkel et al. | |

FOREIGN PATENT DOCUMENTS

| | | |
|---|---|---|
| DE | 1133394 | 7/1962 |
| GB | 1452466 | 10/1976 |

*Primary Examiner* — Clinton Brooks
(74) *Attorney, Agent, or Firm* — N. Denise Brown

(57) ABSTRACT

The present invention relates to a method of producing aromatic amines by hydrogenation of aromatic nitro compounds. This method provides a reactor containing a hydrogenation catalyst; supplies aromatic nitro compounds and hydrogen to the reactor and contacts them with a hydrogenation catalyst, in which the hydrogen which is supplied to the reactor is by a compressor and the compressor contains an operating fluid which at least partially contacts the hydrogen; and regenerates the hydrogenation catalyst by heating and contacting it with oxygen. Particular operating liquids are subsequently exchanged.

10 Claims, No Drawings

METHOD FOR STARTING A REACTION DURING THE PRODUCTION OF AROMATIC AMINES FROM NITROAROMATICS

CROSS-REFERENCE TO RELATED APPLICATION

This application is a National Phase application to PCT/EP2013/057717 filed Apr. 12, 2013 and European Application No.: 12164325.8, filed Apr. 16, 2012.

FIELD OF THE INVENTION

The present invention relates to a method for improved starting-up of the reaction in the preparation of aromatic amines from nitroaromatics, which comprises the steps of provision of a reactor with hydrogenation catalyst present therein, introduction of aromatic nitro compounds and hydrogen into the reactor with contacting of the hydrogenation catalyst, with at least the nitrogen being fed into the reactor by means of a compressor and the compressor containing operating liquid which at least partly contacts the hydrogen, and regeneration of the hydrogenation catalyst by heating and contacting with oxygen. Particular (operating) liquids are subsequently exchanged.

BACKGROUND

Aromatic amines are important intermediates which have to be produced inexpensively and in large amounts. Production plants for aromatic amines are for this reason generally built for very large capacities. The high productivity of these plants is ensured by very long reaction cycles and the problem-free operation between the starting-up and shutting-down operations for the hydrogenation in order to regenerate the hydrogenation catalysts used.

Aniline is an important intermediate, e.g. for the preparation of methylenedi(phenyl isocyanate) (MDI) and is generally prepared on an industrial scale by catalytic hydrogenation of nitrobenzene by means of hydrogen. Particular preference is given to reaction conditions as described in GB 1 452 466 A1, EP 0 011 090 A1 or EP 0 944 578 A2 (isothermal mode of operation) and in EP 0 696 574 B1, EP 0 696 573 B1, EP 1 882 681 A1 (adiabatic mode of operation). Apart from the abovementioned processes having stationary catalyst beds, processes having fluidized catalyst beds have also been described, e.g. in DE 1114820 B, DE 1133394 B or WO 2008034770 A1.

In all the adiabatic and isothermal processes described, the starting material nitrobenzene is reacted with an excess of hydrogen.

The preparation of the aromatic amines is carried out in reaction cycles because the catalytic activity of the hydrogenation catalysts decreases steadily.

The activity of used catalysts for the hydrogenation of aromatic nitro compounds therefore has to be restored at periodic intervals. For this purpose, a regeneration in which carbon-containing deposits are removed from the catalyst by burning-off in a stream of air is carried out. In other embodiments of the process, the burning-off step is followed by a washing step as described in, for example, U.S. Pat. No. 3,684,740. The next reaction cycle can then be started by starting up the hydrogenation plant again. Processes with multiple washing are also described in WO 2012013677 A1.

All the literature references cited do not describe the starting-up process and its difficulties.

In a process for hydrogenating nitro compounds to form the corresponding amines as described in EP 0 944 578 A2 (page 2, lines 1-20), the start-up procedure is discussed. There, it is stated that it is advantageous in terms of the space-time yield to increase the space velocity of aromatic nitro compounds introduced over the catalyst continuously or stepwise to the maximum space velocity over a period of from 10 to 1000 hours.

The quality of a process for hydrogenating aromatic nitro compounds is, firstly, defined by the amount of undesirable by-products of the reaction in the product. Secondly, the quality of a hydrogenation process is defined by the total process of hydrogenation cycle, shutting-down of the hydrogenation, regeneration of the hydrogenation catalyst and start-up of the hydrogenation process being able to be carried out without technical production stoppage.

Although the processes of the prior art which have been described allow aromatic amines having a low content of by-products, which thus, for example, contain only from 50 ppm to 300 ppm of phenols, to be prepared, these by-products always include products which are formed by liberation of ammonia (deamination reaction). This ammonia can react with other compounds (for example $CO_2$) in the reaction system or the offgas lines and form deposits. Separating off ammonia-containing offgas streams and disposing them separately (for example separate introduction into a thermal waste air purification) requires an increased outlay in terms of apparatus and is not always completely possible. The possible problems during start-up of a process for preparing aromatic amines are passed over.

SUMMARY

It was therefore an object of the present invention to provide a process which ensures trouble-free starting-up of the hydrogenation reaction and does not lead to formation of deposits in the reaction apparatuses and the periphery thereof, so that forced shutting-down of the plant does not occur during start-up or after short hydrogenation cycles because of blockages in the reaction apparatuses or the periphery thereof.

This object is achieved according to the invention by a process for preparing aromatic amines by hydrogenation of aromatic nitro compounds, which comprises the steps:
A) provision of a reactor with hydrogenation catalyst present therein;
B) introduction of aromatic nitro compounds and hydrogen into the reactor with contacting of the hydrogenation catalyst, with at least the hydrogen being fed into the reactor by means of a compressor and the compressor containing operating liquid which at least partially contacts the hydrogen;
C) regeneration of the hydrogenation catalyst by heating and contacting with oxygen.
After step C), the steps D1) and/or D2) are carried out:
D1) at least partial removal of liquids which are present in the reactor and/or in plant parts fluidically connected downstream to the reactor and were at least partly present in the reactor and/or in these plant parts during step C);
D2) at least partial replacement of the operating liquid of the compressor which was present in the compressor and/or in recirculation facilities connected to the compressor during step C) by operating liquid which was not present in the compressor and/or in recirculation facilities connected to the compressor during step C).

It has consequently been found, surprisingly, that the reaction spaces and/or the periphery thereof can be at least partially freed of carbon dioxide by replacing liquids present, which were saturated with $CO_2$ in the regeneration process, by fresh liquids. The $CO_2$ is at least partly formed by the burning-off of organic residues on the catalyst.

When the reaction spaces and/or the periphery thereof have been freed of $CO_2$ and the operating liquid in the compressor has been renewed, the following advantages for the start-up procedure for the hydrogenation are obtained:

i) The productivity of the plant increases because the plant does not go down because of blockages in the reaction apparatuses and the periphery thereof, e.g. offgas lines.
ii) The energy costs for repeated start-up are saved.
iii) The product quality does not suffer because of repeated start-up operations.
iv) Cleaning costs for the removal of deposits from the reaction apparatuses and the offgas lines thereof do not occur.

DETAILED DESCRIPTION

The process of the invention therefore achieves the stated object by removing carbon dioxide from the reaction system and the periphery thereof (i.e., for example, the circulating gas compressor) before start-up of the reaction, so that it can no longer contribute to formation of deposits. The start-up of the hydrogenation and the subsequent work-up of the start-up product formed therefore occurs in a technically problem-free manner without downtimes with end product quality which is restricted only once without the need for more product having to be blended as a result of multiple start-ups.

The same of course applies analogously to the ammonia dissolved in the reactor liquids and/or operating liquids of the compressor.

The process of the invention is generally suitable for starting up hydrogenation processes in which the formation of ammonia has to be reckoned with. In particular, it is suitable for starting up hydrogenations as are described in EP 0 944 578 A2, EP 0 011 090 A1, EP 0 696 574 B1, EP 0 696 573 B1, EP 1 882 681 A1, GB 1 452 466 A1, DE 1114820 B, DE 1133394 B or WO 2008034 770 A1. It is particularly suitable if the catalysts as described in U.S. Pat. No. 3,684,740 have been regenerated.

In particular, the process of the invention is particularly suitable when the catalyst contains catalytically active components on an aluminum oxide support having an average diameter of the aluminum oxide particles in the range from 1.0 mm to 7.0 mm and a BET surface area of less than 20 $m^2/g$, and in which the active components comprise at least:
(a) 1-100 g/l of support of at least one metal of groups 8 to 12 of the Periodic Table of the Elements, and
(b) 0-100 g/l of support of at least one transition metal of groups 4 to 6 and 12 of the Periodic Table of the Elements, and also
(c) 0-100 g/l of support of at least one metal of the main group elements of groups 14 and 15 of the Periodic Table of the Elements.

The groups of the Periodic Table of the Elements are cited in this document in accordance with the IUPAC recommendation of 1986.

The aluminum oxide support preferably has an approximately spherical shape and preferably a diameter in the range from 1.0 mm to 7.0 mm.

As regards the mode of operation of the reactor, reaction conditions as described in EP 0 944 578 A2 (isothermal mode of operation) and in EP 0 696 574 B1, EP 0 696 573 B1, EP 1 882 681 A1 (adiabatic mode of operation) are preferred.

Preferred reactors for an isothermally operated reactor are thermostated tube reactors or shell-and-tube reactors. Suitable embodiments of such reactors are described, for example, in DE 2 201 528 A1, DE 2 207 166 A1, DE 198 06 810 A1, EP 1 439 901 A1, EP 1 569 745 A1, EP 1 590 076 A1, EP 1 587 612 A1, EP 1 586 370 A1, EP 1 627 678 A1 or DE 202 006 014 116 U1.

Preferred reactors for an adiabatically operated reactor are those described in DE 10 2006 035 203, paragraphs [0030] to [0033].

It is possible for the catalyst arranged in the reactor to be present in a filter candle through which radial flow occurs. This can be achieved, for example, by the catalyst being retained in a basket which is made up of two concentric cylindrical mesh jackets with fluid-permeable walls. Here, one mesh jacket has a greater radius than the other, which is always referred to as central tube, and the space between the mesh jackets is the reaction space. A bottom of this hollow cylinder is preferably completely closed tightly, while the other is closed only as far as the central tube which is open at this end. The fluid can flow in the radial direction from the outside inward and then be discharged through the central tube. As an alternative, the fluid can also be fed in through the central tube and then flow in a radial direction to the outside where it is then discharged. If this reaction space is located in the same reactor as the isothermal reaction space, it is usually connected in an appropriate manner to the reactor outlet.

The hydrogenation of the nitro compounds is preferably carried out continuously and with recirculation of unreacted hydrogen to the reaction.

The present invention is illustrated with the aid of embodiments. These can be combined with one another in any way as long as the context does not unambiguously indicate the opposite.

In one embodiment of the process of the invention, the compressor is a liquid ring compressor. A liquid ring compressor is frequently also referred to as a water ring pump or liquid ring pump. The functional principle of the liquid ring compressor is based on a star-shaped, eccentrically mounted impeller/rotor which is located in the cylindrical housing of the pump. The operating liquid present in the housing (normally water or condensate) forms a liquid ring which is concentric to the housing and seals the pump chambers during rotation as a result of centrifugal force.

The operating liquid has a number of functions. It is intended to seal, compress, cool and condense. The heat of compression and condensation evolved during compression is removed via the operating liquid. This is for this purpose cooled in the circuit and recirculated.

In a further embodiment of the process of the invention, the operating liquid in the compressor is water or an aqueous solution containing more than 90% by weight of water. For example, in the case of a hydrogenation process for aromatic nitro compounds which uses liquid ring pumps as hydrogen circulating gas compressor the liquid present in the housing (in the hydrogenation of nitroaromatics, the liquid is water) is replaced by fresh liquid before start-up. In a further embodiment of the process of the invention, the reactor is additionally filled or flushed with an inert gas after step C). A suitable inert gas is, in particular, nitrogen.

In a further embodiment of the process of the invention, step D1) is carried out by flushing the reactor and/or plant parts fluidically connected downstream to the reactor with water and/or an aqueous solution containing more than 90% by weight of water (for example condensate).

In a further embodiment of the process of the invention, the molar ratio of hydrogen to nitro groups of the aromatic nitro compounds in step B) is from ≥3:1 to ≤100:1. Preferred ranges of this ratio are from ≥3:1 to ≤10:1 in the case of isothermal process conditions and from ≥60:1 to ≤100:1 in the case of adiabatic process conditions.

In a further embodiment of the process of the invention, aromatic nitro compounds having the general formula (I):

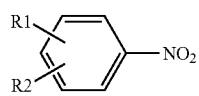

where R1 and R2 are each, independently of one another, hydrogen, methyl or ethyl and R2 can also be $NO_2$, are used in step B). Preferred aromatic amines are nitrobenzene and/or dinitrotoluene, so that the hydrogenation thereof gives aniline or toluenediamine.

In a further embodiment of the process of the invention, the catalyst is arranged in a fixed catalyst bed in the reactor.

In a further embodiment of the process of the invention, the interior of the reactor and/or the interior of plant parts fluidically connected to the reactor is/are heated to a temperature of more than 58° C. after step D1) and/or D2) and before renewed introduction of aromatic nitro compounds and hydrogen into the reactor with contacting of the hydrogenation catalyst. Above this temperature, ammonium carbonate, which can be formed from by-products during the course of the hydrogenation reactions, decomposes into $CO_2$, $NH_3$ and water. This heating thus likewise helps to avoid blockages in the reactor plant and in particular in the offgas system.

The present invention is illustrated with the aid of the following examples, without being restricted thereto.

In the hydrogenation reactions, hydrogen was used in excess (molar ratio of hydrogen/nitrobenzene=6:1). The excess hydrogen was recovered in the condensation of the reaction products and reintroduced into the reaction (circulating gas hydrogen). Consumed hydrogen was replaced by fresh hydrogen. A liquid ring compressor served to circulate the recovered hydrogen. The circulating gas hydrogen contained gaseous impurities. To avoid accumulation of these materials in the circuit, a substream was discharged. This was fed via an offgas system to thermal waste air purification. The condensed reaction products were separated off in a liquid/gas separator (product separator) and collected in a condensate vessel.

After preheating by means of steam, nitrobenzene was vaporized in the stream of hydrogen and thus mixed with the hydrogen. This mixture was then fed into the circulating gas upstream of the reactor. The reactors were constructed as shell-and-tube heat exchangers. The catalyst was located in the tubes. The hydrogenation of nitrobenzene occurs here. A crude aniline/water mixture was formed and left the reactors in gaseous form together with excess hydrogen and was passed to condensation. The shell-and-tube reactor was heated to 240° C. by means of an oil circuit. The plant pressure downstream of the reactor was 1.2 bar(a).

The starting materials nitrobenzene and hydrogen were commercially available materials and had the specifications normal in commerce.

Example 1

Regeneration

After a production cycle, exhausted catalyst having a low residual activity which had been used for the hydrogenation of nitrobenzene to aniline was regenerated by means of a burning-off step. For this purpose, the reaction space was firstly made inert by means of nitrogen and then supplied with a stream of air at about 270° C. in order to burn off carbonaceous deposits. This was carried out until evolution of heat could no longer be observed and the $CO_2$ content of the offgas stream had dropped to less than 0.2% (determined means of IR photometry).

Example 2

Comparative Example

Start-Up and Operation of the Hydrogenation of Nitrobenzene in a Plant after Regeneration of the Hydrogenation Catalyst After regeneration, the reaction apparatuses and the periphery thereof of the reaction system were made inert by means of nitrogen. For this purpose, nitrogen was introduced into the circulating gas system and a purge from the circulating gas into the offgas was operated at the same time until the oxygen concentration in the circulating gas was below 0.5%. The concentration of hydrogen in the circulating gas system was then increased in the same way until the introduction of nitrobenzene and thus the hydrogenation reaction was finally started. The reaction had to be interrupted after 4 days because blockages had occurred in the offgas system. In the cleaning of the offgas system, a white deposit was found. Elemental analysis of the deposit was in agreement with the composition of ammonium carbonate.

Example 3

Example According to the Invention

Start-Up and Operation of the Hydrogenation of Nitrobenzene in a Plant after Regeneration of the Hydrogenation Catalyst After regeneration, the reaction apparatuses and the periphery thereof, e.g. the offgas system, were made inert. The water serving as operating liquid in the liquid ring compressor of the hydrogen circulating gas compressor was replaced by fresh water. The plant was started up as described in example 1. Blockage of the offgas system was not observed and no deposits were found even in a later inspection.

What is claimed is:
1. A process for preparing aromatic amines by hydrogenation of aromatic nitro compounds, which comprises:
A) providing a reactor with hydrogenation catalyst present therein;
B) introducing aromatic nitro compounds and hydrogen into said reactor contacting with said hydrogenation catalyst, wherein at least said hydrogen is fed into the reactor by means of a compressor and said compressor contains an operating liquid which at least partially contacts said hydrogen;
C) regenerating said hydrogenation catalyst by heating and contacting with oxygen;
wherein
D1) at least partially removing liquids which are present in said reactor and/or in plant parts fluidically connected downstream to said reactor and which were at least partly present in said reactor and/or in said plant parts during step C);

and/or:
D2) at least partially replacing said operating liquid of said compressor which was present in said compressor and/or in recirculation facilities connected to said compressor during step C) by an operating liquid which was not present in said compressor and/or in recirculation facilities connected to said compressor during step C);
are carried out after C).

2. The process as claimed in claim 1, wherein said compressor is a liquid ring compressor.

3. The process as claimed in claim 1, wherein said operating liquid in said compressor is water or an aqueous solution containing more than 90% by weight of water.

4. The process as claimed in claim 1, wherein said reactor is additionally filled or flushed with an inert gas after step C).

5. The process as claimed in claim 1, wherein step D1) is carried out by flushing said reactor and/or plant parts fluidically connected downstream to said reactor with water and/or an aqueous solution containing more than 90% by weight of water.

6. The process as claimed in claim 1, wherein the molar ratio of hydrogen to nitro groups of said aromatic nitro compounds in step B) is from ≥3:1 to ≤100:1.

7. The process as claimed in claim 1, wherein aromatic nitro compounds having the general formula (I):

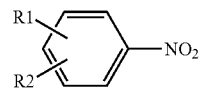

in which:

R1 and R2 are each, independently of one another, hydrogen, methyl or ethyl, with the proviso that R2 can also be $NO_2$, are used in step B).

8. The process as claimed in claim 1, wherein said aromatic nitro compounds in step B) are nitrobenzene and/or dinitrotoluene.

9. The process as claimed in claim 1, wherein the catalyst in said reactor is arranged in a fixed catalyst bed.

10. The process as claimed in claim 1, wherein the interior of said reactor and/or the interior of plant parts fluidically connected to said reactor is/are heated to a temperature of more than 58° C. of step D1) and/or D2) and before renewed introduction of aromatic nitro compounds and hydrogen into said reactor and contacting with said hydrogenation catalyst.

* * * * *